United States Patent [19]

Binder et al.

[11] Patent Number: 4,727,059

[45] Date of Patent: Feb. 23, 1988

[54] FIBRONECTIN SOLUTION SUITABLE FOR USE IN HUMANS AND PROCESS FOR ITS PREPARATION

[75] Inventors: Bernd Binder; Peter Nemeth, both of Vienna, Austria

[73] Assignee: Serotherapeutisches Institut Wien Gesellschaft M.B.H., Vienna, Austria

[21] Appl. No.: 945,095

[22] PCT Filed: Mar. 28, 1986

[86] PCT No.: PCT/AT86/00026

§ 371 Date: Nov. 24, 1986

§ 102(e) Date: Nov. 24, 1986

[87] PCT Pub. No.: WO86/05690

PCT Pub. Date: Oct. 9, 1986

[30] Foreign Application Priority Data

Mar. 28, 1985 [AT] Austria .................................. 933/85

[51] Int. Cl.$^4$ .................. A61K 37/04; A61K 35/16; C07K 15/14
[52] U.S. Cl. ......................................... 514/8; 424/101; 514/21; 530/380; 530/386; 530/392
[58] Field of Search .............. 530/392, 386, 380; 424/101; 514/8, 21

[56] References Cited

U.S. PATENT DOCUMENTS

| | | | |
|---|---|---|---|
| 4,210,580 | 7/1980 | Amrani | 530/392 X |
| 4,305,871 | 12/1981 | Shanbrom | 530/392 X |
| 4,315,906 | 2/1982 | Gelder | 530/386 X |
| 4,341,764 | 7/1982 | Wallace et al. | 530/392 X |
| 4,404,187 | 9/1983 | Schwinn et al. | 424/101 |
| 4,424,206 | 1/1984 | Ohmura et al. | 530/392 X |
| 4,440,679 | 4/1984 | Fernandes et al. | 530/380 X |
| 4,478,829 | 10/1984 | Landaburu et al. | 514/21 |
| 4,560,556 | 12/1985 | Kagitani et al. | 530/380 X |
| 4,565,651 | 1/1986 | Ohmura et al. | 530/392 |
| 4,585,654 | 4/1986 | Landaburu et al. | 424/101 |
| 4,587,122 | 5/1986 | Kagitani et al. | 424/101 |
| 4,623,717 | 11/1986 | Fernandes et al. | 530/380 |

FOREIGN PATENT DOCUMENTS 0035204  9/1981  European Pat. Off. .
0047216  3/1982  European Pat. Off. .
0124018  11/1984  European Pat. Off. .

*Primary Examiner*—Howard E. Schain
*Attorney, Agent, or Firm*—Karl F. Ross; Herbert Dubno

[57] ABSTRACT

A fibronectin injectable solution is made by recovering a fibronectin-containing raw material which is solubilized, provided with stabilizers and then subjected to an initial heat treatment at 57° to 60° for at least ten hours. After fibronectin concentration and the addition of further stabilizers and plasma-protein vehicle, the solution is again subjected to a temperature of 60° for ten hours to provide an injectable solution which is free from virulent hepatitis.

2 Claims, No Drawings

FIBRONECTIN SOLUTION SUITABLE FOR USE IN HUMANS AND PROCESS FOR ITS PREPARATION

CROSS REFERENCE TO RELATED APPLICATIONS

This application is a national phase application corresponding to PCT/AT86/00026 filed Mar. 28, 1986 and based, under the International Convention, on an Austrian application No. A 933/85 of Mar. 28, 1985.

FIELD OF THE INVENTION

The invention relates to a fibronectin solution suitable for use in humans and a process for the preparation thereof.

BACKGROUND OF THE INVENTION

Fibronectin is a high-molecular glycoprotein, consisting of two subunits, each having a molecular weight of approximately 220,000 and which is found in plasma in soluble form, in a concentration of about 0.3 mg/ml. In insoluble form, fibronectin is found in connective tissues and as associated with basement membranes. Soluble fibronectin interacts with collagen, heparin, fibrin and staphilococci; it has a function in cell adhesion, as for instance thrombocyte adhesion, the structuring of fibrin coagulation, and in the formation of connective tissue, but also particularly as one of the main opsonizing factors in the phagocytosis function of the reticuloendothelial system.

Fibronectin is cross-linked with fibrin under the action of factor XIII and stabilizes the fibrin coagulation, attracting fibroblasts in the process. Corresponding to its incorporation in the fibrin coagulum, the serum concentration of fibrin is lower by approximately 20°–50° than that of plasma.

Of particular clinical importance is the opsonin-function of fibronectin, and there are clear indications that, for the normal function of the reticuloendothelial systems in the spleen, the liver and the bone marrow, fibronectin is required. So, for instance, in research with laboratory animals it has been established that after artificial fibronectin depletion, phagocytosis capacity is massively inhibited. Further, fibronectin facilitates the bond between fibrin and macrophages and increases the phagocytosis in streptococci. A lower level of fibronectin is found in patients, after major surgery or trauma and in the case of advanced malignancies. The reduction of fibronectin is probably also related to the "shock lung" occuring in septicemia. In patients in intensive care it has been found that a higher level of fibronectin, established on arrival, could usually be connected to a significantly lower mortality rate, and that patient whose fibronectin level fell below 0.195 mg/ml during their stay, presented a mortality rate higher by 65% than that of patients whose fibronectin level did not fall below 0.195% during their stay.

Fibronectin is present in fresh plasma, fresh frozen plasma, antihemophilic plasma and cryoprecipitates, and has been used therapeutically in the form of cryoprecipitates, whereby in some of the patients dramatic improvements took place, particularly with regard to cardio-pulmonary functions. This mode of administrating fibronectin has however the disadvantage of a quite large volume and of the fact that these forms of administration can not be subjected to heat treatments analogous to those which make albumin safe from hepatitis.

OBJECT OF THE INVENTION

It is the object of this invention to create a preparation of fibronectin in the form of a solution containing fibronectin, which has been made virus-safe through heat inactivation of hepatitis and other possible viral contaminants.

DESCRIPTION OF THE INVENTION

In the process according to the invention for the preparation of this fibronectin solution inorganic in that the initial material containing fibronectin in the form of cryoprecipitate, fresh frozen plasma, outdated plasma, cryoprecipitate-poor plasma or fibronectin-containing human plasma fractions, or for instance made from plasma precipitated with organic precipitating agents, such as polyethyleneglycol, alcohols, ether, or with anorganic precipitating agents, such as ammonium sulfate, sodium sulfate, sodium chloride, or from chromatographically produced fibronectin-containing plasma fractions (for instance ion-exchange chromatography or affinity chromatography on gelatine-, heparin-, or arginine sepharose) is subjected to fractionating stages, and to the so-obtained untreated fibronectin preparation at least one stabilizer is added. This product then is treated with heat at a temperature of at least 50° C., for the separation of fibronectin, and then again subjected to pasteurization at a temperature of at least 60° C. for at least 10 hours. The so-obtained fibronectin-containing supernatant is then concentrated and freed from the electrolytes and the low-molecular weight peptides. The so-obtained fibronectin solution is then processed into a preparation which can be intravenuously administered to humans, through the addition of further solvents, such as albumin, plasmaprotein.

By contrast with heretofore-known forms of administration, the fibronectin solution according to the invention is a heat-inactivated fibronectin preparation which contains, for instance, 2 mg/ml fibronectin in its dimeric form dissolved in a 5%-plasmaprotein solution. In spite of the heat-inactivation of any virus contained therein, this preparation maintains it full function (potency) regarding the linkage to collagen and fibrin, the mediation in adhesion of macrophages and the increase of the phagocytosis rate of macrophages. The adhesion of macrophages, as well as the phagocytosis rate is influenced depending on the dosage in the case of the preparation according to the invention, whereby with a concentration of 100 μg/ml an increase of the adhesion by approximately 90% and an increase in the phagocytosis rate by over 70% is reached. In preclinical research, this preparation was tolerated without side effects by five patients, in the highest tested concentration of 1 ml/kg with an infusion speed of 2 ml/min.

SPECIFIC EXAMPLE

The invention is illustrated by the following example:

Human plasma from healthy donors is diluted with purified water to a protein concentration of 3.8% and treated with saturated solution of ammonium sulfate up to a saturation of 25–28%. The pH-value is 6.3 or 8.0.

The ammonium-sulfate precipitate is dissolved at room temperature in a solution of sodium citrate, 0.06 mol/liter, mixed with the same amount of saturated sodium-chloride solution.

The so-formed precipitate is again dissolved at room temperature in a 0.06 mol solution of sodium citrate, and stabilized with 0.02 mol/liter of sodium caprylate and 0.02 mol/liter of sodium-N-acetyl-DL-tryptophanate at a pH-value of 7.6 to 8.0. Than it is mixed with a solution of 50 g glucose per liter. A 10-hour long pasteurization follows, at a temperature of 57°–60° C.

After the separation of the resulting precipitate, the clear fibronectin containing supranatant is diafiltered, in order to eliminate the electrolytes and peptides with a molecular weight under 20,000 dalton. Subsequently, the fibronectin is concentrated with the same ultrafilter. The fibronectin concentrate is mixed with plasma-protein solution for clinical purposes, and stabilized with 0.03 mol/liter sodium caprylate and with 0.01 mol/liter sodium-N-acetyl-DL-tryptophanate. An isotonic coefficient of the solution is established through the addition of sodium chloride (Na-content 130–160 mol/liter). The pH-value is set at 7.0±0.3.

The final product is filled into the corresponding containers, where it is pasteurized for 10 hours at 60° C.

The fibronectin-containing plasma-protein solutions suited for use in humans, in accordance with the invention, can have, for instance, the following compositions, wherein the individual components are given in g/l:

|  | A | B | C |
| --- | --- | --- | --- |
| Overall protein content wherein | 49.23 | 53.30 | 48.40 |
| (a) albumin | 44.75 | 48.18 | 41.19 |
| (b) fibronectin | 0.97 | 1.05 | 0.81 |
| (c) thermo-stable globulin | 3.51 | 4.07 | 6.40 |
| Sodium chloride | 8.48 | 8.19 | 5.42 |
| sodium caprylate | 4.99 | 4.99 | 4.99 |
| sodium-N—acetyl-DL-tryptophanate | 2.68 | 2.68 | 2.68 |

We claim:

1. A process for producing an injectable fibronectin solution, consisting essentially of the steps of:
   (a) collecting a fibronectin-containing raw material in the form of cryoprecipitate, fresh frozen plasma, cryoprecipitate-poor plasma, fibronectin-containing human plasma fraction, plasma precipitated by inorganic or organic precipitating agent or chromatographically separated fibronectin-containing plasma fractions, and subjecting said fibronectin-containing raw material to a preliminary separation to recover an initial fibronectin-containing solution;
   (b) stabilizing said initial fibronectin-containing solution with sodium citrate, sodium caprylate, sodium-N-acetyl-DL-tryptophanate, and glucose to form an additive-stabilized fibronectin-containing solution;
   (c) heat treating said additive-stabilized fibronectin-containing solution at a temperature of 57° C. to 60° C. for a period of at least 10 hours and recovering a fibronectin-containing supernatant;
   (d) ultrafiltering said supernatant to eliminate electrolytes and peptides with a molecular weight below 20,000 daltons and concentrating fibronectin in said supernatant by ultrafiltration to form a fibronectin-containing concentrate;
   (e) mixing said concentrate with plasma protein and stabilizing the resulting plasma-protein solution with sodium caprylate and sodium-N-acetyl-DL-tryptophanate, and adjusting the stabilized plasma-protein solution to substantially isotonic Na concentration and a pH of substantially 7.0; and
   (f) heating the solution resulting from step (e) at 60° C. for a period of 10 hours to form an injectable fibronectin solution free from hepatitis virulence.

2. An injectable fibronectin solution as made by the process of claim 1.

* * * * *